(12) United States Patent
Cavallini et al.

(10) Patent No.: US 7,445,124 B2
(45) Date of Patent: Nov. 4, 2008

(54) FILTER

(75) Inventors: Paolo Cavallini, Cavezzo (IT);
Hakvoort Koos, Emmen (NL); Bernd Mathieu, Spiesen (DE)

(73) Assignee: Fresenius HemoCare Deutschland GmbH, Bad Homburg (DE)

( * ) Notice: Subject to any disclaimer, the term of this patent is extended or adjusted under 35 U.S.C. 154(b) by 526 days.

(21) Appl. No.: 10/537,055

(22) PCT Filed: Dec. 2, 2003

(86) PCT No.: PCT/EP03/13596

§ 371 (c)(1),
(2), (4) Date: Jun. 2, 2005

(87) PCT Pub. No.: WO2004/050147

PCT Pub. Date: Jun. 17, 2004

(65) Prior Publication Data

US 2006/0049097 A1    Mar. 9, 2006

(30) Foreign Application Priority Data

Dec. 2, 2002    (DE)    ................................ 102 56 160

(51) Int. Cl.
*B01D 35/00*    (2006.01)
*B01D 35/30*    (2006.01)

(52) U.S. Cl. ........................ 210/485; 210/435; 210/445; 210/484

(58) Field of Classification Search ................. 210/435, 210/445, 483, 484
See application file for complete search history.

(56) References Cited

U.S. PATENT DOCUMENTS

| | | | |
|---|---|---|---|
| 3,506,130 A | 4/1970 | Shaye | |
| 4,976,861 A * | 12/1990 | Pall | ............................ 210/508 |
| 2003/0209479 A1* | 11/2003 | Lynn et al. | ................ 210/257.1 |
| 2004/0251195 A1 | 12/2004 | Oka et al. | |

FOREIGN PATENT DOCUMENTS

| | | |
|---|---|---|
| EP | 0 526 678 B2 | 2/1993 |
| EP | 0 953 361 A1 | 11/1999 |
| EP | 1 300 168 A1 | 4/2003 |
| JP | 0 726 7871 | 10/1995 |
| WO | WO 95/17237 | 6/1995 |
| WO | WO 01/91880 A1 | 12/2001 |
| WO | WO 02/04045 A1 | 1/2002 |

\* cited by examiner

*Primary Examiner*—Krishnan S. Menon
*Assistant Examiner*—Benjamin Kurtz
(74) *Attorney, Agent, or Firm*—Jacobson Holman PLLC

(57) ABSTRACT

A filter, in particular for the separation of leucocytes from further blood components, has an outer sheath, at least one intermediate layer which is a component of a frame or which forms a frame, an inlet chamber which is in communication with an inlet for the medium to be filtered, an outlet chamber which is in communication with an outlet for the filtrate, and a filter material which separates the inlet chamber from the outlet chamber. The filter is particularly low in dead space and can be centrifuged in a simple manner since the filter material is encompassed between the outer sheath and the intermediate layer.

14 Claims, 3 Drawing Sheets

Detail C

Detail B

Section A-A ic
FILTER

CROSS-REFERENCE TO RELATED APPLICATION

This is a nationalization of PCT/EP03/013596 filed Dec. 2, 2003 and published in German.

BACKGROUND OF THE INVENTION

1. Field of Invention

The present invention relates to a filter, in particular for the separation of leucocytes from further blood components, having an outer sheath, having at least one intermediate layer which is a component of a frame or forms a frame, having an inlet chamber which is in communication with an inlet for the medium to be filtered and an outlet chamber which is in communication with an outlet for the filtrate, and having a filter material which separates the inlet chamber from the outlet chamber.

Filters of this kind are, for example, used to liberate blood or blood components from leucocytes prior to storage or to transfusion to the recipient, since said leucocytes can cause unwanted side effects. There is therefore a necessity to separate leucocytes and, optionally, further interfering materials prior to the storage or transfusion of the blood or of its components (e.g. erythrocytes, plasma).

2. Description of the Prior Art

Filters of this kind are known in numerous different embodiments. The filter disclosed in EP 0 526 678 B2 has an outer sheath made of flexible material which is connected to an intermediate layer of two soft foils which form a frame. The filter material which separates the outlet chamber of the filter from the inlet chamber is received in the frame. The filter material is welded into the frame formed by the foils and has the effect in this manner that the blood to be filtered or the blood components to be filtered only have to flow through the filter surface to enter into the outlet chamber.

An embodiment of a filter is known from WO 01/91880 A1, wherein the outer sheath consists of two foils which are directly welded to one another. No intermediate layer is provided. The filter has in inwardly disposed welding seam and an outwardly disposed welding seam, with the outwardly disposed welding seam directly connecting the foils forming the outer sheath to one another and the inwardly disposed welding seam connecting the filter material to the outer sheath. A non-welded region comprising a filter medium is located between the two welding seams and is resilient due to the lack of a welding seam and damage during centrifuging can be largely avoided by means of it. The filter known from WO 01/91880 A1 has the disadvantage that it has stubs on both oppositely disposed sides of the outer sheath for the inlet of the blood and for the outlet of the filtrate respectively, whereby a flat surface is prevented on both sides of the filter which would be desired for the purpose of centrifuging.

There is a disadvantage with the filter apparatus known from EP 0 526 678 B2 in that dead spaces in which no blood can be filtered arise in the region of the frame encompassing the filter material. This is unwanted because, on the one hand, the available filter volume is not fully used. On the other hand, there is a disadvantage in that valuable blood components can accumulate in the dead spaces which cannot be regained or can only be regained with difficulty after the end of the filtration. The accompanying loss of blood components not regained is unwanted.

SUMMARY OF THE INVENTION

It is therefore the object of the present invention to further develop a filter of the kind initially named such that it opens up the possibility of a simple centrifuging and such that the probability for the occurrence of dead spaces is reduced.

This object is solved by a filter as described herein. Accordingly, the filter material is encompassed between the outer sheath and the intermediate layer. The advantage is achieved by the connecting of the filter material to a side of the outer sheath that the occurrence of dead spaces can be prevented at least on this side and the available space of the filter is used correspondingly better. Furthermore, at least one contact side of the filter can be made without stubs, which is of advantage for the centrifuging.

The advantage further results over the aforesaid EP 0 526 678 B2 due to the design of the filter in accordance with the invention that the filter in accordance with the invention can consist of three layers, of which one forms the intermediate layer and two form the outer sheath, whereas the filter disclosed in the named printed document consists of at least four layers, namely of two intermediate foils to fix the filter material in place and of two layers forming the outer sheath. The filter in accordance with the present invention can generally also have more than three layers.

The intermediate layer is a component of the frame encompassing the filter material or forms the frame and has the advantage that, due to the number of welded layers, the welding seams can be made comparatively soft, whereby damage during the centrifuging can largely be avoided. The filter material extends in the recess formed by the frame.

If the intermediate layer is only a component of a frame, the further frame components, i.e. the further sections fixing the filter material in place or encompassing it, are formed, for example, by the outer sheath. In an aspect of the invention of this kind, the arrangement of the filter material between the intermediate layer and the outer sheath in accordance with the invention is accordingly only provided regionally. The arrangement of the filter material between the intermediate layer and the outer sheath in accordance with the invention thus does not have to be present in the whole filter periphery region, but can also only be provided for partial regions, for example for the region of the outlet.

The shape of the intermediate layer can be any desired one and can be selected freely depending on the existing demands. It is, for example, feasible to design the intermediate layer in the form of a straight or curved strip, in U shape, in the form of a semi-circle, etc., or also in a peripheral manner, whereby a closed frame is created.

To avoid damage during centrifuging, it is advantageous for the filter to have an outer sheath consisting of flexible material.

The outer sheath can consist of two parts, in particular foils, which are welded to one another, with the filter material being encompassed between one of these parts and the intermediate layer. In a preferred aspect of the invention, the outer sheath and/or the intermediate layer consist of PVC.

It is particularly advantageous for the filter material to be encompassed between the outer sheath on the inlet side and the intermediate layer.

The filter material can be welded to the outer sheath and to the intermediate layer.

In an advantageous aspect of the invention, the intermediate layer consists of flexible material.

A first inwardly disposed welding seam can be provided which connects the filter material to the intermediate layer and to the outer sheath, and a second outwardly disposed welding seam can be provided which connects the intermediate layer to the outer sheath. The inwardly disposed welding seam fixes the filter material in place in this manner between the intermediate layer and the outer sheath. The outwardly disposed welding seam connects the intermediate layer to the outer sheath.

In an embodiment of this kind, the marginal region of the filter material is preferably arranged in a region which extends between both welding seams around the filter material. It is particularly advantageous for the intermediate layer to have one or more apertures which connect the marginal region of the filter material encompassed in the frame to the inlet chamber and the outlet chamber. Such apertures bring along the advantage that no or comparatively little material remains in this region of the filter material, but flows from there either into the outlet chamber or back into the inlet chamber and can be filtered again. The loss of e.g. blood or blood components can be minimized in this manner.

The aperture(s) of the intermediate layer is/are preferably arranged in a region between the first and second welding seams. It can be achieved in this manner that the filtered medium, in particular blood, preferably flows, starting from this region, into the outlet chamber. With a corresponding design of the apertures, it is likewise possible to guide the filtered blood back into the inlet chamber and to filter it again.

In accordance with a further aspect of the present invention, a plurality of intermediate layers are provided. In this case, the filter has four or more layers of which e.g. two form the outer sheath and e.g. two are made as intermediate layers. More than four layers can also be used. The risk of damage during centrifuging is reduced if more layers are welded to one another. The softness and resilience of the welding seams and thus of the filter can be increased by the number of intermediate layers.

It is particularly advantageous for the outer sheath to consist of two foils welded to one another. They can be directly welded to one another or can receive one or more intermediate layers between them.

In a further aspect of the present invention, provision is made for the filter material to be elliptic in its plan view. This aspect permits an optimum filter utilization by a uniform distribution of blood on the filter material. Furthermore, the occurrence of dead zones can be largely avoided by an elliptic design.

The inlet for the medium to be filtered, for example for the concentrate of erythrocites, can consist of a stub welded to the outer sheath which consists of two limbs arranged at right angles to one another and of which the limb welded to the outer sheath substantially extends perpendicular from the outer sheath.

The outlet can consist of a cylindrical stub which is welded to the outer sheath and/or to the intermediate layer and whose longitudinal axis extends in a plane which extends parallel to the plane formed by the filter material and is offset with respect to it. The outlet stub is thus arranged "asymmetrically". It can be welded between the outer sheath and the intermediate layer or also directly between two foils forming the outer sheath.

It is particularly advantageous for the filter material to be pressed or needled. A design of the filter material of this kind reduces the filter volume with an unchanged filter mass and thus increases the filter density. This has the advantage that the stability of the filter medium is in particular increased during the centrifuging. Furthermore, the regaining of blood from the filter is improved due to the lower volume with an unchanged filter performance.

Further details and advantages of the present invention will be explained in more detail with reference to an embodiment shown in the drawing. There are shown:

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
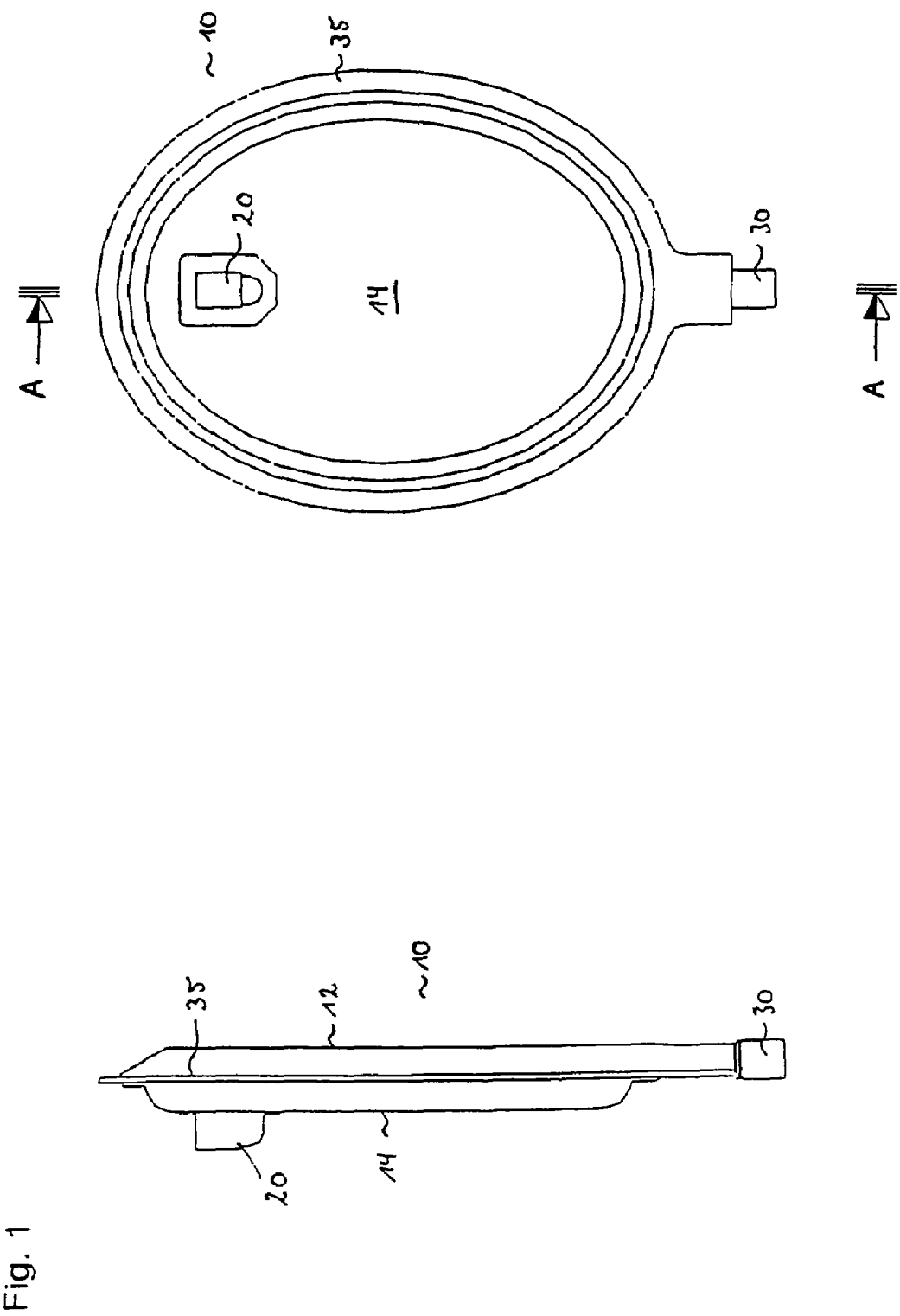
FIG. 1: a side view and a plan view of the leucocyte filter in accordance with the invention.

FIG. 1 shows the leucocyte filter 10 in accordance with the invention in a side view. It has an outer sheath consisting of the foils 12, 14. The foils 12, 14 are made in flexible form and consist of PVC. The outer foil 14 is welded to the inlet stub 20 which has two limbs which are arranged at right angles to one another and of which the limb welded to the foil 14 extends perpendicular thereto, whereas the other limb extends substantially parallel to the outer foil 14.

Furthermore, the outlet stub 30 is provided which is substantially cylindrical. It is welded to the outer foil 12 and to a foil 16 forming an intermediate layer (see FIG. 3, detail B).

The foils 12, 14 are welded at their periphery to the intermediate layer 16, whereby an outwardly disposed welding seam 35 is formed.

As can be seen from FIG. 1, the longitudinal axis of the stub 30 is not located in the plane of the welding seam 35, but in a plane which extends parallel to it and which is offset with respect to the plane of the welding seam 35.

It can be seen from the plan view of the leucocyte filter in accordance with FIG. 1, right hand illustration, that it has an elliptic shape. The inlet stub 20 is not arranged at the center of the elliptic region, but—in accordance with FIG. 1—above it. The elliptic design of the filter permits an ideal distribution of the medium to be filtered, whereby the filter is largely utilized. In addition, dead zones can be largely avoided.

Figure 2:
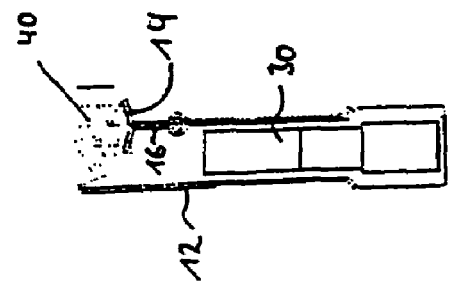
FIG. 2: a sectional representation in accordance with section line A-A in FIG. 1.
Figure 2:
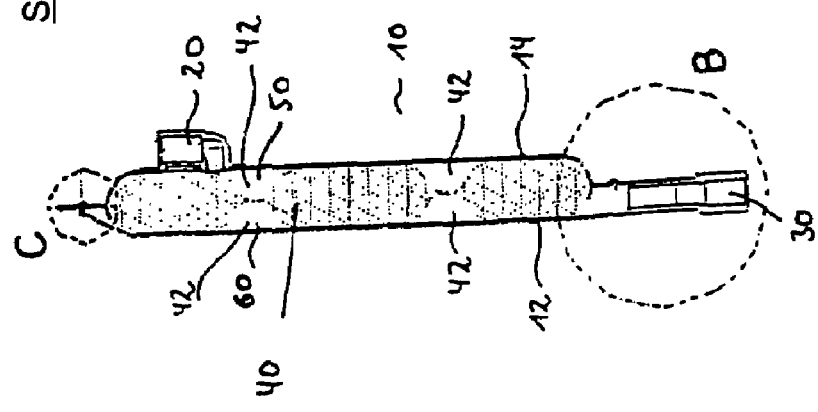

FIG. 2 shows the sectional representation of the leucocyte filter in accordance with the sectional line A-A in FIG. 1. The arrangement of the filter material 40 can be seen from this which separates the inlet side 50, into which the medium to be filtered flows after exiting the inlet stub 20, from the outlet side 60, into which the filtrate flows through the filter and exits through the stub 30. The filter material 40 consists of polybutylene terephthalate fibers which can be coated. The filter material 40 can be made in multilayers.

The filter material 40 is a pressed or needled filter element which should be indicated in a schematic manner by the recesses 42. A filter element of this kind has the advantage that its mechanical stability is increased, which is in particular necessary for the purpose of centrifuging. A further advantage consists of the fact that the regaining of the medium located in the filter material is facilitated. The filter performance is not negatively influenced by the reduced volume of the filter material. The amount of the filter material remains identical with respect to a non-pressed or non-needled embodiment.

Figure 3:
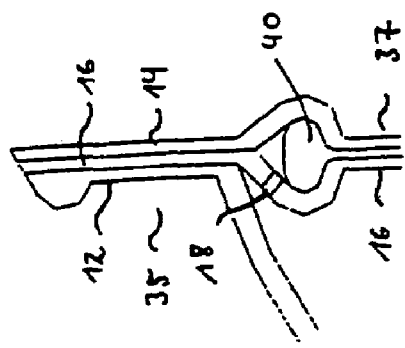
FIG. 3: an enlarged representation of detail B and detail C in FIG. 2.

FIG. 3 shows the details B and C in accordance with FIG. 2. Detail B relates to the region of the outlet stub 30 which is welded between the outer foil 12 and the intermediate foil 16 welded to the outer foil 14. The outlet stub 30 extends parallel to the longitudinal axis of the elliptically made filter. As can in particular be seen from FIG. 2, the outlet stub 30 is arranged at the lowest point of the outlet chamber 60 so that it can be fully emptied. As can in particular be seen from FIG. 2, a substantially flat support of the filter can be formed in this manner which is formed in the present case by the outer foil 12.

As can likewise be seen from FIG. 2 and detail B in FIG. 3, the central axis of the cylindrical outlet stub 30 is not located in the plane which is formed by the filter material 40, but is made offset thereto.

An enlarged view of the upper end region of the filter 10 can be seen from Figure C. The outer foil 14, the filter material 40 and the intermediate foil 16 are shown here which are welded to one another by means of a first, inwardly disposed welding seam 37. Furthermore, the second, outwardly disposed welding seam 35 can be seen which connects the foils 12 and 14 to the intermediate foil 16. The marginal zone of the filter material 40 is located between these welding seams. As can be seen from detail C, the intermediate foil 16 has a recess 18 which connects the marginal region of the filter material 40 to the outlet chamber. It is thereby achieved that blood or blood components can also be regained from this marginal region of the filter material 40. As can be seen from FIG. 3, the filter material 40 is welded between the foil 14 forming the outer sheath on the inlet side and the intermediate layer 16. The advantage thereby results that the filter is made free of dead space on the inlet side since the filter material 40 is welded directly to the outer foil 14, as can also be seen from FIG. 2.

The following example illustrates the influence of the apertures of the intermediate layer in accordance with the invention and the treatment of the filter material:

EXAMPLE 1

35 cm$^2$ filter area, 26 layers of coated PBT (average diameter 2 µm, surface density 50 g/m$^2$); design of the welding seams in accordance with FIGS. 1-3:
WBC (white blood cells): fewer than 200,000/RCC (red cell concentrate) unit;
Filtration time: 10-13 minutes;
RCC yield: 93%.

EXAMPLE 2

The filter corresponds to the filter of Example 1, but in the non-needled or pressed state of the filter material;
WBC: 200,000-400,000;
Filtration time: 15-17 minutes;
RCC yield: 89%.

EXAMPLE 3

The filter corresponds to the filter of Example 1, but without apertures of the intermediate layer;
WBC: fewer than 200,000/RCC unit;
Filtration time: 10-13 minutes;
RCC yield: 91%.

Figure 4:
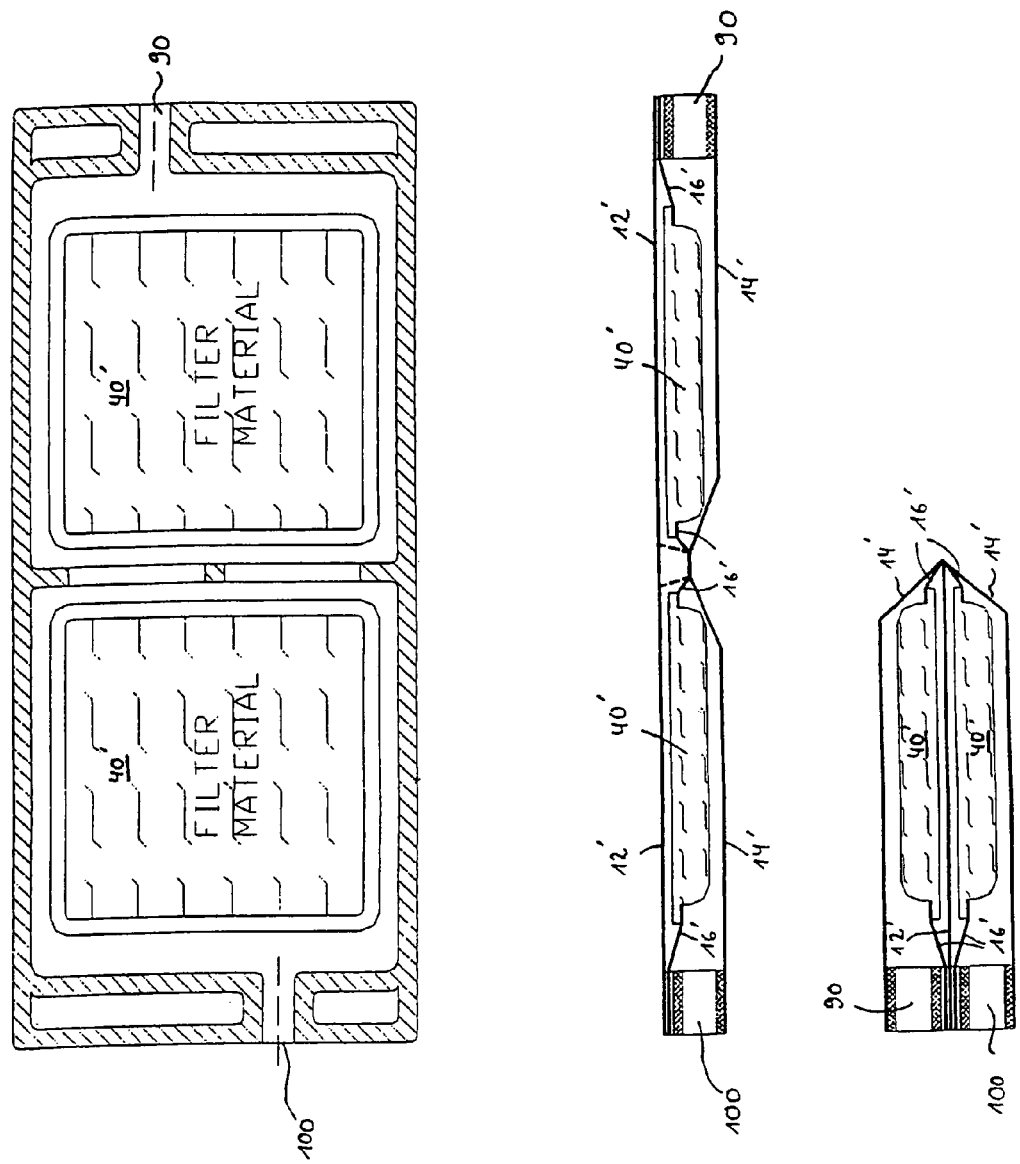
FIG. 4: different representations of a further embodiment of a filter in accordance with the invention.

FIG. 4 shows a further embodiment of the present invention in different views in which the joining of the marginal region of the filter material to the intermediate layer is shown in simplified form.

In the embodiment in accordance with FIG. 4, two filter media 40' arranged in series are provided. They are welded in their marginal regions to a foil 16' made as an intermediate layer. The foil 16' is furthermore welded to the foils 12' and 14' which form the outer sheath of the filter.

The medium to be filtered flows through the inlet stub 90 which is also cylindrical like the outlet stub 100 and first flows through the filter material 40' shown on the right from the bottom to the top. From there, the medium is guided through corresponding recesses on the upper side of the filter material 40' arranged on the left hand side, flows through it and is finally removed through the outlet stub 100.

The foils 12', 14' forming the outer sheaths and also the foil 16' forming the intermediate layer are made of PVC.

The filter shown in FIG. 4 is symmetrical and can be folded about a central axis, as is reproduced in FIG. 4, lower illustration. In this state, the filter can be centrifuged particularly advantageously.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A filter, in particular for the separation of leucocytes from further blood components, comprising an outer sheath, at least one intermediate layer which is a component of a frame or which forms a frame, an inlet chamber in communication with an inlet for a medium to be filtered, an outlet chamber in communication with an outlet for a filtrate, a filter material which separates the inlet chamber from the outlet chamber and which is encompassed between the outer sheath and the intermediate layer, a first inwardly disposed welding seam which connects the filter material to the intermediate layer and to the outer sheath, and a second outwardly disposed welding seam which connects the intermediate layer to the outer sheath.

2. The filter in accordance with claim 1, wherein the outer sheath is made of flexible material.

3. The filter in accordance with claim 1, wherein the outer sheath comprises a first foil and a second foil welded to one another, and wherein the filter material is encompassed between one of the foils and the intermediate layer.

4. The filter in accordance with claim 1, wherein the filter material is encompassed between the outer sheath on an inlet side and the intermediate layer.

5. The filter in accordance with claim 1, wherein the filter material is welded to the outer sheath and to the intermediate layer.

6. The filter in accordance with claim 1, wherein the intermediate layer is constructed of flexible material.

7. The filter in accordance with claim 1, wherein the intermediate layer has one or more apertures which connect a region of the filter material encompassed in the frame to at least one of the inlet chamber and the outlet chamber.

8. The filter in accordance with claim 7, wherein the apertures are arranged in a region between the first and second welding seams.

9. The filter in accordance with claim 1, wherein a plurality of intermediate layers are provided.

10. The filter in accordance with claim 1, wherein the filter material is elliptic in shape in plan view.

11. The filter in accordance with claim 1, wherein the inlet includes a stub which is welded to the outer sheath and which has a first limb and a second limb arranged at right angles to one another, with the limb welded to the outer sheath extending substantially perpendicular from the outer sheath.

12. The filter in accordance with claim 1, wherein the outlet includes a cylindrical stub which is welded to at least one of the outer sheath and the intermediate layer and which has a longitudinal axis extending in a plane parallel to a plane formed by the filter material and being offset with respect to the plane of the filter material.

13. The filter in accordance with claim 1, wherein the filter material is pressed.

14. The filter in accordance with claim 1, wherein the filter material is needled.

* * * * *